(12) United States Patent
Galano et al.

(10) Patent No.: US 10,444,221 B2
(45) Date of Patent: Oct. 15, 2019

(54) METHOD OF TRANSFERRING A REAGENT CARD FROM A CARD TRAVEL SURFACE OF AN AUTOMATED ANALYZER TO A WASTE RECEPTACLE

(71) Applicant: Siemens Healthcare Diagnostics Inc., Tarrytown, NY (US)

(72) Inventors: Kenneth Galano, Wrentham, MA (US); Michael Parker, Uxbridge, MA (US); Aaron Sung-Lien Tang, Boston, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 15/434,509

(22) Filed: Feb. 16, 2017

(65) Prior Publication Data

US 2017/0160297 A1    Jun. 8, 2017

Related U.S. Application Data

(62) Division of application No. 13/712,144, filed on Dec. 12, 2012, now Pat. No. 9,606,103.

(60) Provisional application No. 61/576,394, filed on Dec. 16, 2011.

(51) Int. Cl.
*G01N 35/10* (2006.01)
*G01N 33/487* (2006.01)
*G01N 35/00* (2006.01)

(52) U.S. Cl.
CPC ... *G01N 33/4875* (2013.01); *G01N 35/00029* (2013.01); *G01N 35/10* (2013.01); *G01N 2035/00039* (2013.01); *G01N 2035/00148* (2013.01); *Y10T 436/110833* (2015.01)

(58) Field of Classification Search
None
See application file for complete search history.

(56) References Cited

U.S. PATENT DOCUMENTS

| | | | |
|---|---|---|---|
| 3,123,443 | A | 3/1964 | Smeby |
| 3,212,855 | A | 10/1965 | Mast et al. |
| 3,716,348 | A | 2/1973 | Perkins |
| 3,814,668 | A | 6/1974 | Blake et al. |

(Continued)

FOREIGN PATENT DOCUMENTS

JP    2002257837 A  *  9/2002

*Primary Examiner* — Christopher Adam Hixson
*Assistant Examiner* — Michelle Adams
(74) *Attorney, Agent, or Firm* — Dunlap Codding P.C.

(57) ABSTRACT

An automated analyzer for reagent cards having a leading end, a trailing end and a length between the leading end and the trailing end comprises a travel surface assembly having a card travel surface and an edge. A test analyzing mechanism is adjacent to the travel surface, and a waste receptacle is adjacent to the edge below the travel surface. The waste receptacle has a side and a waste cavity. A ramp member positioned below the travel surface has an end and a sloped surface, and is movable between an extended position where the sloped surface extends into the waste cavity, and a retracted position where the end is spaced from the side a distance greater than the length of the reagent card. A moving mechanism operably coupled with the ramp member is configured to move the ramp member between the extended position and the retracted position.

6 Claims, 9 Drawing Sheets

(56) References Cited

U.S. PATENT DOCUMENTS

| | | |
|---|---|---|
| 4,526,753 A | 7/1985 | Boger et al. |
| 5,242,659 A | 9/1993 | Wurschum |
| 5,670,375 A | 9/1997 | Seaton et al. |
| 6,024,921 A * | 2/2000 | Freiner .................... B01L 3/50 422/66 |
| 7,220,385 B2 * | 5/2007 | Blecka ............... G01N 35/0099 422/561 |
| 2007/0264157 A1 | 11/2007 | Takagi et al. |

* cited by examiner

METHOD OF TRANSFERRING A REAGENT CARD FROM A CARD TRAVEL SURFACE OF AN AUTOMATED ANALYZER TO A WASTE RECEPTACLE

INCORPORATION BY REFERENCE

This application is a Division of U.S. Ser. No. 13/712,144, filed on Dec. 12, 2012, which claims priority to U.S. Provisional Application Ser. No. 61/576,394, filed on Dec. 16, 2011. Both applications are incorporated by reference herein in their entirety.

BACKGROUND

The inventive concepts disclosed herein generally relate to analyzers for multiple-profile reagent cards, and more particularly, but not by way of limitation, to a waste ramp configured to stack used reagent cards during the operation of automated reagent card analyzers.

To satisfy the needs of the medical profession as well as other expanding technologies, such as the brewing industry, chemical manufacturing, etc., a myriad of analytical procedures, compositions, and tools have been developed, including the so-called "dip-and-read" type reagent test devices. Regardless of whether dip-and-read test devices are used for the analysis of a biological fluid or tissue, or for the analysis of a commercial or industrial fluid or substance, the general procedure involves a test device coming in contact with the sample or specimen to be tested, and manually or instrumentally analyzing the test device.

Dip-and-read reagent test devices can be manufactured at relatively low cost and are very convenient for individuals to use. Consequently dip-and-read reagent test devices enjoy wide use in many analytical applications, especially in the chemical analysis of biological fluids, because of their relatively low cost, ease of usability, and speed in obtaining results. In medicine, for example, numerous physiological functions can be monitored merely by dipping a dip-and-read reagent test device into a sample of body fluid or tissue, such as urine or blood, and observing a detectable response, such as a change in color or a change in the amount of light reflected from, or absorbed by the test device.

Many of the dip-and-read reagent test devices for detecting body fluid components are capable of making quantitative, or at least semi-quantitative, measurements. Thus, by measuring the detectable response after a predetermined time, a user can obtain not only a positive indication of the presence of a particular constituent in a test sample, but also an estimate of how much of the constituent is present. Such dip-and-read reagent test devices provide physicians and laboratory technicians with a facile diagnostic tool, as well as with the ability to gauge the extent of disease or of bodily malfunction.

Illustrative of dip-and-read reagent test devices currently in use are products available from Siemens Healthcare Diagnostics Inc. under the trademark MULTISTIX, and others. Immunochemical, diagnostic or serological test devices, such as these usually include one or more carrier matrix, such as absorbent paper, having incorporated therein a particular reagent or reactant system which manifests a detectable response (e.g., a color change) in the presence of a specific test sample component or constituent. Depending on the reactant system incorporated with a particular matrix, these test devices can detect the presence of glucose, ketone bodies, bilirubin, urobilinogen, occult blood, nitrite, and other substances. A specific change in the intensity of color observed within a specific time range after contacting the dip-and-read reagent test device with a sample is indicative of the presence of a particular constituent and/or its concentration in the sample. Some other examples of dip-and-read reagent test devices and their reagent systems may be found in U.S. Pat. Nos. 3,123,443; 3,212,855; and 3,814,668.

However, dip-and-read reagent test devices suffer from some limitations. For example, dip-and-read reagent test devices typically require a technician to manually dip the test device into a sample, wait for a prescribed amount of time, and visually compare the color of the test device to a color chart provided with the test device. This process is slow and the result reading is skill-dependent (e.g., exact timing, appropriate comparison to the color chart, ambient lighting conditions, and technician vision) and may be inconsistent between two different technicians performing the same test. Finally, the act of manually dipping the test device into the sample may introduce cross-contamination or improper deposition of the test sample on the test device, such as via incomplete insertion of the test device into the sample, insufficient time for the sample to be deposited onto the test device, or having too much sample on the test device which may drip, leak, or splash on the technician's work area, person, or clothing.

Testing tools and methods have been sought in the art for economically and rapidly conducting multiple tests, especially via using automated processing. Automated analyzer systems have an advantage with respect to cost per test, test handling volumes, and/or speed of obtaining test results or other information over manual testing. One such automated analyzer system is the CLINITEK ATLAS urinalysis system available from Siemens Healthcare Diagnostics.

Automated instruments which are currently available for instrumentally reading individual dip-and-read reagent test devices, or reagent strips, (e.g., CLINITEK STATUS reflectance photometer, manufactured and sold by Siemens Healthcare Diagnostics, Inc.) require each dip-and-read reagent test device to be manually loaded into the automated instrument after contacting the test device with specimen or sample to be tested. Manual loading requires that the reagent test device be properly positioned in the automated instrument within a limited period of time after contacting the solution or substance to be tested. At the end of the analysis, used test devices are removed from the instrument and disposed of in accordance with applicable laws and regulations.

Traditional dip-and-read test devices were designed with manual use in mind and are not particularly well suited for use with highly automated instruments, due to their small size and limited number of tests per each test device. A different test device format is presently used in the CLINITEK ATLAS automated urinalysis system, which is manufactured and sold by Siemens Healthcare Diagnostics. The CLINITEK ATLAS instrument uses a cassette containing reagent areas mounted seriatim on a continuous plastic substrate which is wound into a reel rotatably housed in the cassette. While the reagent cassette is well suited for automation, the manufacturing cost for this type of format amounts to eight times that of the dip-and-read reagent test device format described above.

Another recent development is the introduction of multiple-profile reagent cards and multiple-profile reagent card automated analyzers. Multiple-profile reagent cards are essentially card-shaped test devices which include multiple reagent-impregnated matrices or pads for simultaneously or sequentially performing multiple analyses of analytes, such as the one described in U.S. Pat. No. 4,526,753, for example. Multiple-profile reagent cards result in an efficient, economical, rapid, and convenient way of performing automated analyses. An automated analyzer configured to use multiple-profile reagent cards typically takes a multiple-profile reagent card, such as from a storage drawer, or a cassette, and advances the multiple-profile reagent card through the analyzer over a travelling surface via a card moving mechanism. The moving mechanism may be a conveyor belt, a ratchet mechanism, a sliding ramp, or a card-gripping or pulling mechanism, for example. As the multiple-profile reagent card is moved or travels along the travelling surface, one or more pipettes (e.g., manual or automatic) may deposit one or more samples or reagents onto one or more of the matrices or pads on the multiple-profile reagent card. Next, the multiple-profile reagent card may be analyzed (e.g., manually or automatically) to gauge the test result, such as via an optical imaging system, a microscope, or a spectrometer, for example. Finally, the used card is removed from the analyzer, and is disposed of in an appropriate manner.

However, as multiple-profile reagent cards are relatively rapidly moved through the automated analyzer, there is a need for an efficient method of collecting and disposing of used multiple-profile reagent cards. For example, used multiple profile reagents cards may contain harmful or hazardous chemical or biological agents, and may pose a risk of cross-contamination if handled or disposed of improperly. Further, the high-volume throughput of automatic analyzers may result in a large number of multiple-profile reagent cards that need to be removed from the automatic analyzer, which may cause downtime for the automatic analyzer, or an increased workload for technicians or other personnel, for example.

SUMMARY

In one aspect, the inventive concepts disclosed herein are directed to an automated analyzer for reagent cards having a leading end, a trailing end, and a length between the leading end and the trailing end. The analyzer comprises a travel surface assembly having a card travel surface and an edge and a test analyzing mechanism adjacent to the card travel surface. A waste receptacle is positioned adjacent to the edge and below the card travel surface, the waste receptacle having a side spaced a distance away from the edge greater than the length of the reagent card, and a waste cavity. A ramp member is positioned below the card travel surface, the ramp member having an end, a sloped surface and being movable between an extended position where the sloped surface extends beyond the edge of the card travel surface and into the waste cavity such that the end of the ramp member is spaced from the side of the waste receptacle a distance less than the length of the reagent card, and a retracted position where the end of the ramp member is spaced from the side of the waste receptacle a distance greater than the length of the reagent card. A moving mechanism is operably coupled with the ramp member and is configured to move the ramp member between the extended position and the retracted position.

In another aspect, the inventive concepts disclosed herein are directed to a method, comprising advancing a first reagent card having a first leading end and a first trailing end along a card travel surface of an automated analyzer and past an edge of the card travel surface so that the first reagent card falls onto a sloped surface of a ramp member positioned within a waste cavity of a waste receptacle. The method further includes moving the ramp member out of the waste cavity such that the first reagent card slides off the sloped surface, and advancing a second reagent card having a second leading end and a second trailing end along the card travel surface and past the edge of the card travel surface so that the second reagent card falls onto the sloped surface of the ramp member. The method further includes moving the ramp member out of the waste cavity such that the second reagent card slides off the sloped surface and onto the first reagent card to stack the second reagent card on the first reagent card.

In yet another aspect, the inventive concepts disclosed herein are directed to a method, comprising attaching a ramp member to a mover assembly of an automated analyzer such that the mover assembly is configured to simultaneously advance a reagent card along a card travel surface and extend the ramp member into a waste cavity of a waste receptacle.

BRIEF DESCRIPTION OF THE DRAWINGS

To assist those of ordinary skill in the relevant art in making and using the inventive concepts disclosed herein, reference is made to the appended drawings and schematics, which are not intended to be drawn to scale, and in which like reference numerals are intended to refer to the same or similar elements for consistency. For purposes of clarity, not every component may be labeled in every drawing. Certain features and certain views of the figures may be shown exaggerated and not to scale or in schematic in the interest of clarity and conciseness. In the drawings.

DETAILED DESCRIPTION

Figure 1:
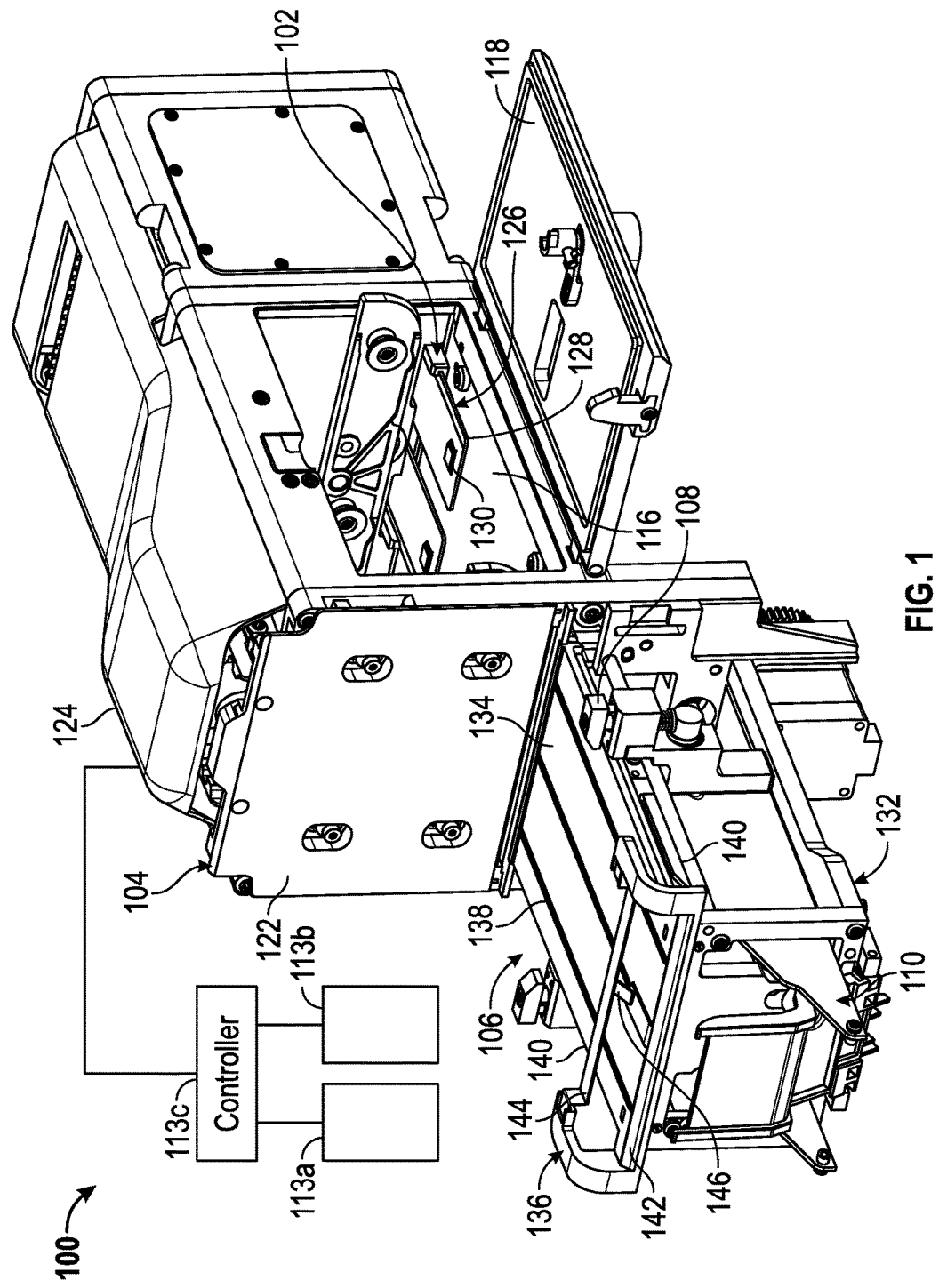
FIG. 1 is a perspective view of an exemplary automated analyzer including an exemplary embodiment of a waste ramp assembly according to the inventive concepts disclosed herein with a ramp member of the waste ramp assembly shown in a partially extended position.

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. The inventive concepts disclosed herein are capable of other embodiments or of being practiced or carried out in various ways. Also, it is to be understood that the phraseology and terminology employed herein is for the purpose of description and should not be regarded as limiting the inventive concepts disclosed and claimed herein in any way.

In the following detailed description of embodiments of the inventive concepts, numerous specific details are set forth in order to provide a more thorough understanding of the inventive concepts. However, it will be apparent to one of ordinary skill in the art that the inventive concepts disclosed herein may be practiced without these specific details. In other instances, well-known features have not been described in detail to avoid unnecessarily complicating the instant disclosure.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherently present therein.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Further, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Finally, as used herein qualifiers such as "about," "approximately," and "substantially" are intended to signify that the item being qualified is not limited to the exact value specified, but includes some slight variations or deviations therefrom, caused by measuring error, manufacturing tolerances, stress exerted on various parts, wear and tear, and combinations thereof, for example.

The inventive concepts disclosed herein are generally directed to a retractable waste ramp assembly positioned below and configured to extend laterally beyond an edge of a travel surface of an automatic analyzer, on which multiple-profile reagent cards (hereinafter referred to as "reagent cards" or "cards") are advanced. The waste ramp assembly includes a ramp member that is movable between an extended position and a retracted position, such that when the ramp member is substantially extended, a used reagent card may fall off the edge of the travel surface and onto the ramp member as the used reagent card is advanced beyond the edge of the travel surface. Gravity may cause the used reagent card to fall onto the extended ramp member, for example. The ramp member may then be retracted substantially under the travel surface such that the used reagent card slides off the ramp member and falls substantially flat in a waste receptacle (e.g., a container). The waste receptacle may be removable from the automatic analyzer, so that the used reagent cards can be discarded.

Optionally, the waste ramp assembly may include a comb which may be pivotably connected to a base, such that the comb may extend above the ramp member when the ramp member is in the extended position, to engage a trailing end of a used reagent card as the used reagent card lands on the ramp member. The comb may prevent the used reagent card from sliding back up the ramp member and over the edge of the travel surface as the ramp member is moved to the retracted position. Once the ramp member is mostly or fully retracted, the comb may also be retracted, such that the reagent card is allowed to fall into the waste receptacle so that the reagent card lies flat into the waste receptacle. The waste receptacle may be positioned sufficiently below the ramp member, such that when two or more used reagent cards are stacked onto one another, the used reagent cards are positioned substantially below the bottom of the ramp member so as not to interfere with the movement of the ramp member, for example.

While the inventive concepts disclosed herein will be described primarily in connection with automatic analyzers using multiple-profile reagent cards, the inventive concepts disclosed herein are not limited to automatic analyzers or to multiple-profile reagent cards. For example, a ramp member according to the inventive concepts disclosed herein may be implemented with a manual analyzer, or may be implemented with an automatic analyzer using a dip-and-read reagent test device, or a reel of reagent test substrate, and combinations thereof, as will be appreciated by a person of ordinary skill in the art having the benefit of the instant disclosure.

Figure 2:
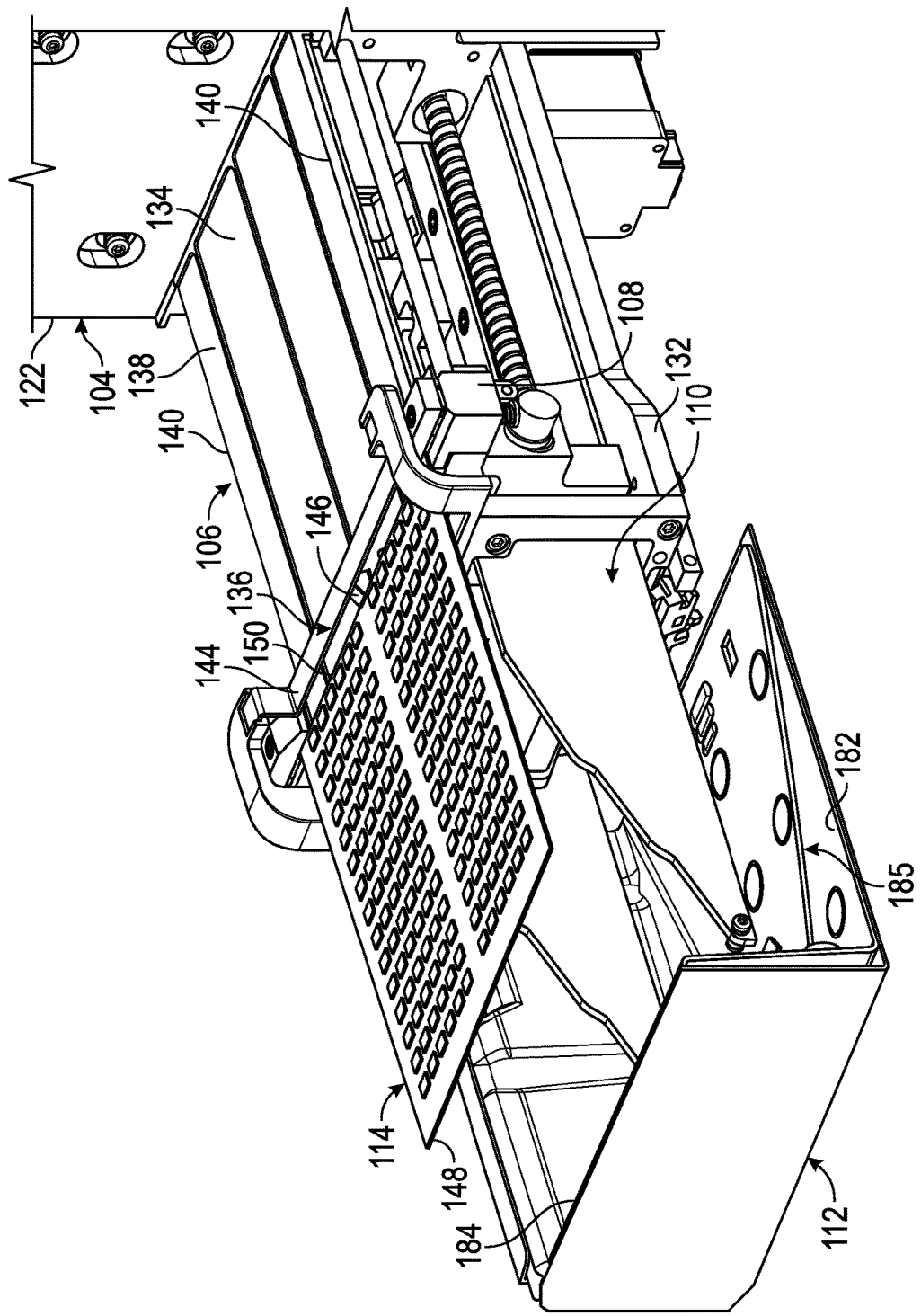
FIG. 2 is a partial perspective view of the analyzer of FIG. 1, with a multiple-profile reagent card shown extending partially past an edge of a travel surface of the analyzer according to the inventive concepts disclosed herein.

Referring now to FIGS. 1-2, an exemplary embodiment of an automatic analyzer 100 is shown therein. The automatic analyzer 100 may include a storage compartment 102 including a gate assembly 104, a travel surface assembly 106, a mover assembly 108, a waste ramp assembly 110, and a waste receptacle 112 (FIG. 2). An optional external housing (not shown) may be implemented to house and protect the various components of the automatic analyzer 100, and to protect technicians and laboratory work surfaces from contamination, for example.

Some exemplary embodiments of the analyzer 100 may include one or more test analyzing mechanisms 113a such as optical imagers, spectrophotometers, gas chromatographs, microscopes, IR sensors, and combinations thereof, for example, configured to gauge test results as one or more multiple-profile reagent card 114 is advanced through the analyzer 100. The reagent card 114 may have a leading end, a trailing end, and a length therebetween, and may include one or more reagent pads attached thereto. Further, some exemplary embodiments may include one or more sample delivery mechanisms 113b, such as an automatic pipette operated by a robotic arm, a manual pipette, and combinations thereof, in order to deposit a sample onto the reagent card 114. The test analyzing mechanism 113a and the sample delivery mechanism 113b may be controlled and read by one or more controller 113c, for example.

The storage compartment 102 may be configured to receive and store one or more reagent cards 114 therein, such that the one or more reagent cards 114 may be stripped or removed from the storage compartment 102 one at a time and may be advanced over the travel surface assembly 106 as will be described below. The storage compartment 102 may be configured to receive and hold a stack of reagent cards 114 therein, or may be configured to receive a cartridge (not shown), or a cassette (not shown) containing one or more reagent card 114 for example. The storage compartment 102 is shown as being substantially rectangular in shape, but it is to be understood that a storage compartment 102 according to the inventive concepts disclosed herein may have any desired size and shape, and may hold any desired number of reagent cards 114 therein, for example.

The storage compartment 102 may include a gate assembly 104, a bottom 116, and a door 118.

The door 118 may be any suitable member that may be opened and closed to access the interior of the storage compartment 102, as will be readily appreciated by a person of ordinary skill in the art having the benefit of the instant disclosure.

The gate assembly 104 may include a gate 122 operably coupled with a gate raising mechanism 124, for example. The gate 122 is shown as forming a part of the storage compartment 102, such that the gate 122 may be selectively opened and closed by the gate raising mechanism 124 to allow one or more reagent cards 114 to be advanced out of the storage compartment 102 and over the travel surface assembly 106. In some exemplary embodiments, the gate 122 may be configured as a vapor and/or moisture barrier, protecting the inside of the storage compartment 102 from moisture and contamination, for example. The gate 122 may be operated by any suitable mechanism, such as the gate raising mechanism 124, which may be manual or automatic, such as a gear mechanism, a servo, an electrical motor, an actuator, and combinations thereof, for example. In some exemplary embodiments a computer processor executing processor executable code may operate the gate raising mechanism 124 to raise and lower the gate 122, and to operate an optional card-stripping mechanism 126 to advance one or more reagent cards 114 past the gate 122. The computer processor (not shown) may be operatively coupled with the controller 131*c*, for example.

The optional card-stripping mechanism 126 may extend at least partially into the storage compartment 102, and may be configured to strip, eject, advance, or otherwise remove a reagent card 114 from the storage compartment 102 (e.g., from a cassette or from a stack of reagent cards 114), and advance such reagent card 114 at least partially past the gate 122. In some exemplary embodiments, the card-stripping mechanism 126 may be configured to advance one or more reagent card 114 out of the storage compartment 102 and at least partially or substantially completely past the gate 122, when the gate 122 is at least partially raised or open. In some exemplary embodiments, the gate 122 may be lowered onto the reagent card 114 as the reagent card 114 is partially advanced out of the storage compartment 102. The card-stripping mechanism 126 may be implemented as any suitable mechanism such as a conveyor belt, or a movable plate 128 having a card-stripping protrusion 130 formed therein, and combinations thereof, for example.

It is to be understood that in some exemplary embodiments of the inventive concepts disclosed herein, the card-stripping mechanism 126 may be omitted and one or more reagent card 114 may be advanced past the gate 122 in any desired manner, such as via gravity, conveyor belt, spring-loaded ejection mechanism, ratchets, manually, and combinations thereof. Further, in some exemplary embodiments of the inventive concepts disclosed herein the storage compartment 102 may be omitted, and reagent cards 114 may be introduced onto the travel surface assembly 106 in any suitable manner, including being manually inserted or fed into the analyzer 100, being provided in a roll, or combinations thereof.

The mover assembly 108 may be a conveyor belt, a ratchet mechanism, a sliding ramp, or a card-gripping or pulling mechanism, for example. As the reagent card 114 is moved or travels along the travel surface 134, one or more pipettes (e.g., manual or automatic) of the sample delivery mechanism 113*b* may deposit one or more samples or reagents onto the reagent card 114, and then the reagent card 114 may be read by the test analyzing mechanism 113*a*, for example.

The travel surface assembly 106 may be supported by a support 132 and may include a travel surface 134 and card retainer assembly 136.

The support 132 may be configured to support the travel surface assembly 106 and to optionally house and support other assemblies and components of the analyzer 100 (e.g., the mover assembly 108) as will be described herein below, for example. The support 132 may be constructed of any desired material such as plastics, metals, or non-metals, for example, and by any desired technique, as will be readily appreciated by a person of ordinary skill in the art having the benefit of the instant disclosure.

The travel surface 134 may include one or more optional ridges 138, two sides 140, and an edge 142. The travel surface 134 may be implemented as a substantially flat travel surface 134 configured to allow a reagent card 114 to travel thereon, such as via sliding onto or over the travel surface 134, for example. The travel surface 134 may extend substantially horizontally adjacent to the gate 122, such that a reagent card 114 advanced past the gate 122 may be advanced or otherwise travel over the travel surface 134. In some exemplary embodiments, the travel surface 134 may extend at least partially into the storage compartment 102, such as by being at least partially defined by the bottom 116 of the storage compartment 102 so that the gate 122 may be lowered onto the travel surface 134. In some exemplary embodiments, the travel surface 134 and the reagent card 114 and the travel surface 134 may be sized so that a portion of the reagent card 114 may extend a distance past one or more sides of the travel surface 134, as will be described below.

It is to be understood that in some exemplary embodiments the travel surface 134 may be angled at any desired angle, and/or may have any desired curvature (e.g., concave or convex), as will be appreciated by persons of ordinary skill in the art having the benefit of the instant disclosure.

The travel surface 134 may be constructed of any desired material, such as plastics, metals, non-metals, thermoset materials, glass, resins, and combinations thereof, for example. The travel surface 134 may be constructed using any desired technique such as injection molding, casting, machining, 3D printing, and combinations thereof, for example.

One or more optional ridges 138 may be formed in the travel surface 134 and may be configured to allow a reagent card 114 to slide thereon, such that the contact surface area between the reagent card 114 and the travel surface 134 may be reduced to reduce friction. It is to be understood that while three ridges 138 are shown in FIGS. 1-2, the inventive concepts disclosed herein may be implemented with any number of ridges 138, such as a single ridge 138, two ridges 138, or more than three ridges 138. Further, in some exemplary embodiment, the one or more ridges 138 may be omitted, for example. The one or more ridges 138 may have rounded or smooth surfaces, and may be coated with any desired friction-reducing coating material or combination of materials, such as nickel polytetrafluoroethylene, for example.

The two sides 140 may be implemented as tabs, for example, and the travel surface 134 may be sized so that a reagent card 114 positioned onto the travel surface 134 extends at least partially laterally from the sides 140 so as to be grasped by the mover assembly 108 as will be described below, for example.

The edge 142 can be configured to allow a reagent card 114 to fall therefrom, and may have any desired cross-sectional shape such as being a 90° edge, or may be tapered at any desired angle, such as an angle varying between about 0° and about 90°, for example. The edge 142 is shown as extending substantially angled relative to the travel surface 134, but it is to be understood that in some exemplary embodiments of the inventive concepts disclosed herein, the edge 142 may be substantially perpendicular or may be angled at any desired angle relative to the travel surface 134, such as an angle varying from about 45° to about 135°.

The card retainer assembly 136 may be connected to the support 132 or to the travel surface 134 and may include a spring 144 extending over the travel surface 134 and having a tab 146.

The card retainer assembly 136 may be connected to the support 132 or to the travel surface 134 in any suitable manner, such as via brackets, bolts, adhesives, seams, joints, tabs, bolts, and combinations thereof. In some exemplary embodiments, the card retainer assembly 136 and the travel surface 134 may be formed as a unitary component. Further, in some exemplary embodiments, the card retainer assembly 136 may be omitted.

The spring 144 may be spaced a distance from the travel surface 134, such that a reagent card 114 may pass between the spring 144 and the travel surface 134, for example. The spring 144 may be constructed of any suitable material, such as steel, titanium, metals, non-metals, resilient plastics, and combinations thereof.

The tab 146 may extend from the spring 144 and may come into contact with the travel surface 134 at about the middle of the spring 144, for example. The tab 146 may be angled relative to the travel surface 134 at any desired angle, such as an angle varying from about 0° to about 90°, for example. The tab 146 may be configured to slightly compress a reagent card 114 against the travel surface 134, as the reagent card 114 travels between the 144 and the travel surface 134. A portion of the reagent card 114 may be configured so as to slide between the tab 146 and the travel surface 134 as the reagent card 114 is advanced over the travel surface 134, for example. The tab 146 may be constructed of any suitable resilient material, such as stainless steel, titanium, metal, non-metals, resilient plastics, and combinations thereof, for example.

It is to be understood that while the tab 146 is shown as having a generally rectangular cross-section, in some exemplary embodiments of the inventive concepts disclosed herein, the tab 146 may have any desired cross-section, such as being oval, triangular, irregular, and combinations thereof. Further, in some embodiments more than one tab 146 may be implemented, or the tab 146 may be omitted, for example.

In some exemplary embodiments, the card retainer assembly 136 may be positioned adjacent to or close to the edge 142 of the travel surface 134 and may be spaced a distance from the edge 142, such that a reagent card 114 having a leading end 148 (see FIG. 2) partially advanced past the edge 142 may be retained on the travel surface 134 so long as a trailing end 150 of the reagent card 114 has not advanced past the tab 146. The tab 146 may compress the trailing end 150 of the reagent card 114 against the travel surface 134 so as to prevent the reagent card 114 from falling off the edge 142. Once the trailing end 150 is advanced past the tab 146, the reagent card 114 may fall off the edge 142 by way of gravity, for example.

Figure 3:
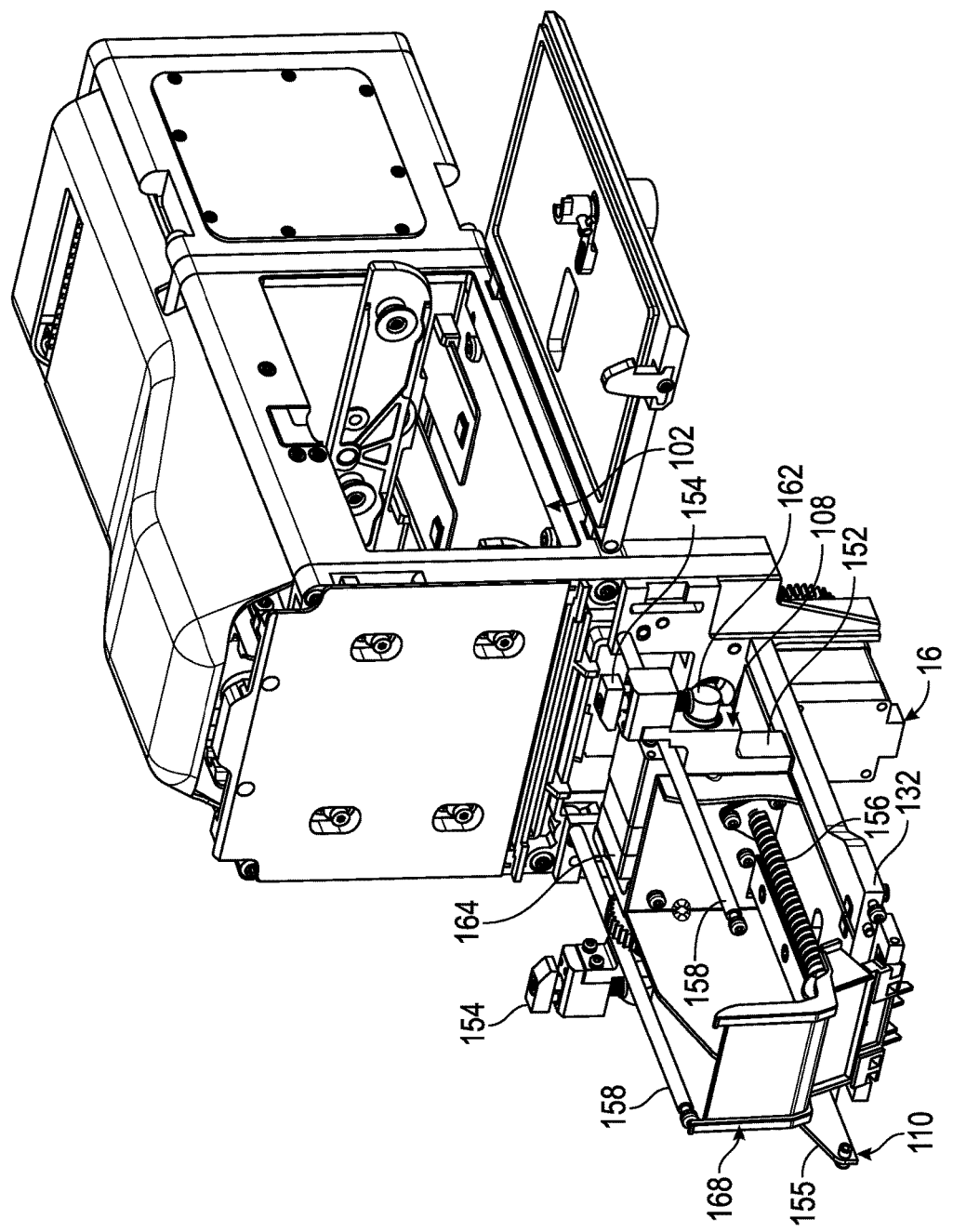
FIG. 3 is a partial perspective view of the analyzer of FIG. 1, with a portion the ramp member shown in a partial cutout view, for clarity.

Referring now to FIG. 3, the mover assembly 108 may include a movable carriage 152, and one or more clamps 154 attached to the carriage 152. The waste ramp assembly 110 includes a ramp member 155 attached to the carriage 152.

The carriage 152 may be at least partially positioned in the support 132 below the travel surface 134, and may be implemented as any suitable device that is movably connected to the support 132 in a controlled manner. The carriage 152 can be configured to move relative to the support 132 so that the one or more clamps 154 and the ramp member 155 may be moved laterally relative to the travel surface 134 from the gate 122 towards the edge 142, and from the edge 142 towards the gate 122, for example.

In some exemplary embodiments, the carriage 152 may be movably connected to the support via a threaded shaft 156 and guide rods 158. A motor 160 may be operably coupled with the carriage 152 or with the threaded shaft 156 so that the carriage 152 may be moved along the guide rods 158 via the threaded shaft 156 as the motor 160 is actuated. As will be appreciated by a person of ordinary skill in the art, the motor 160 may rotate the threaded shaft 156 relative to the carriage 152 in some exemplary embodiments. The carriage 152 may be moved along the threaded shaft 156 in this manner, such that the carriage 152 may be moved bi-directionally relative to the travel surface 134, for example.

Further, as will be appreciated by a person of ordinary skill in the art, the threaded shaft 156, and the motor 160 may be omitted, and any other desired moving mechanism configured to move the carriage 152 relative to the support 132 may be implemented, such as an actuator, a pneumatic motor, a belt driven mechanism, a ratcheting mechanism, a magnetic actuator, a gear-driven mechanism, a hydraulic actuator, and combinations thereof.

The one or more clamps 154 may extend at least partially above the travel surface 134 and may be positioned adjacent to the sides 138 of the travel surface 134. The one or more clamps 154 may be implemented as any suitable device configured to contact or clamp a portion of one or more reagent card 114. One or more card-retentions features (not shown) may be implemented with the clamps 154, such as roughened surfaces, teeth, protrusions, bumps, ridges, striation, knurls, spikes, ratchets, and combinations thereof, for example, to aid the one or more clamps 154 to securely engage the reagent card 114.

The clamps 154 may be connected with the carriage 152 via cams 162 configured to bias (e.g., via springs) the clamps 154 in a closed position, and to be rotated via a clamping mechanism 164 so as to open the clamps 154, for example. The clamping mechanism 164 may be connected to the carriage 152 such that the clamping mechanism 164 moves with the carriage 152, and so that the clamping mechanism 164 functions substantially independently from the carriage 152, for example. It is to be understood that the clamping mechanism 164 may be implemented as any suitable clamping mechanism 164 configured to selectively open and close the clamps 154 so that the clamps 154 may engage, or clamp, or disengage, or unclamp a reagent card 114, so as to move the reagent card 114 along the travel surface 134, for example.

Figure 4:
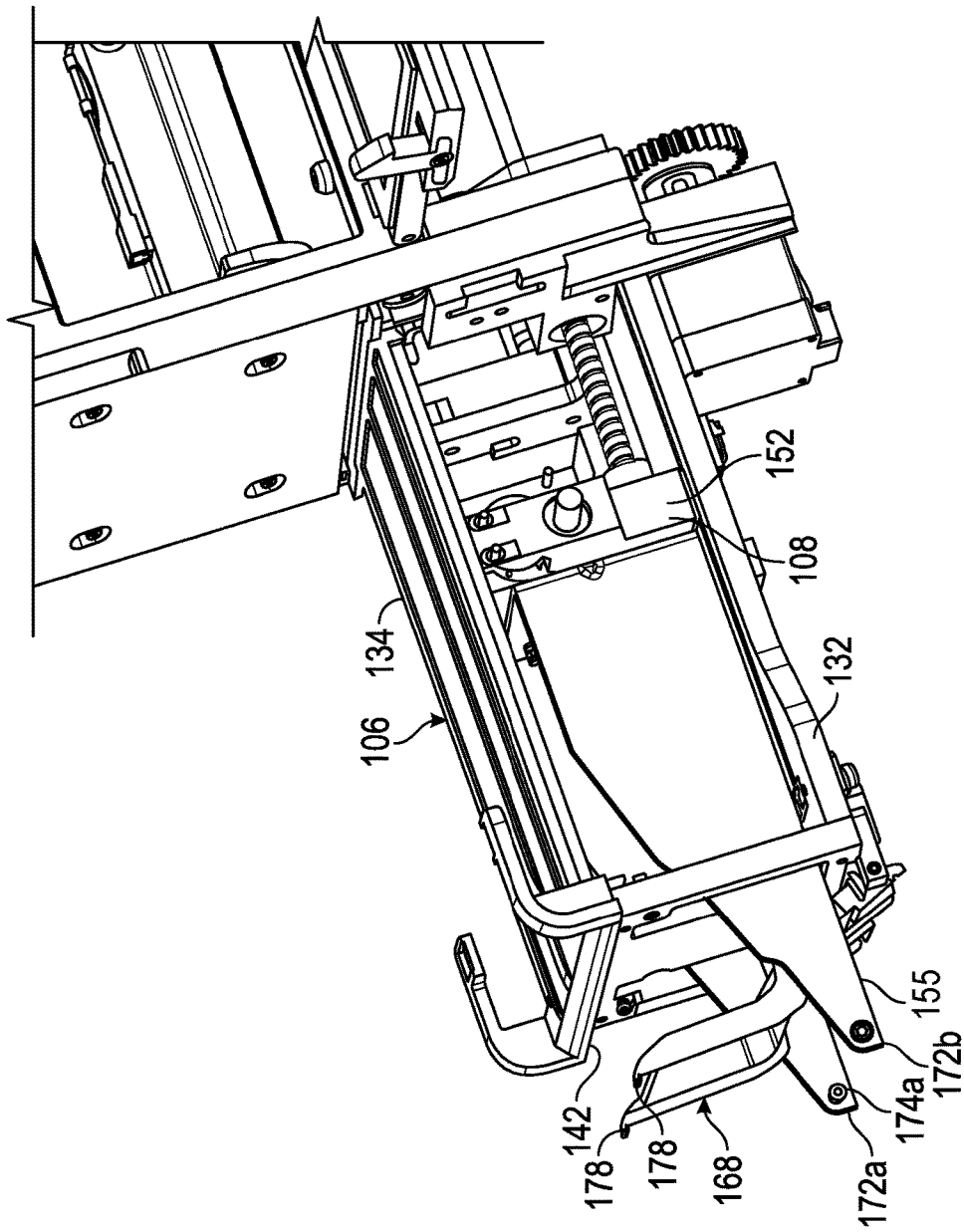
FIG. 4 is a partial perspective view of the analyzer of FIG. 1.
Figure 5:
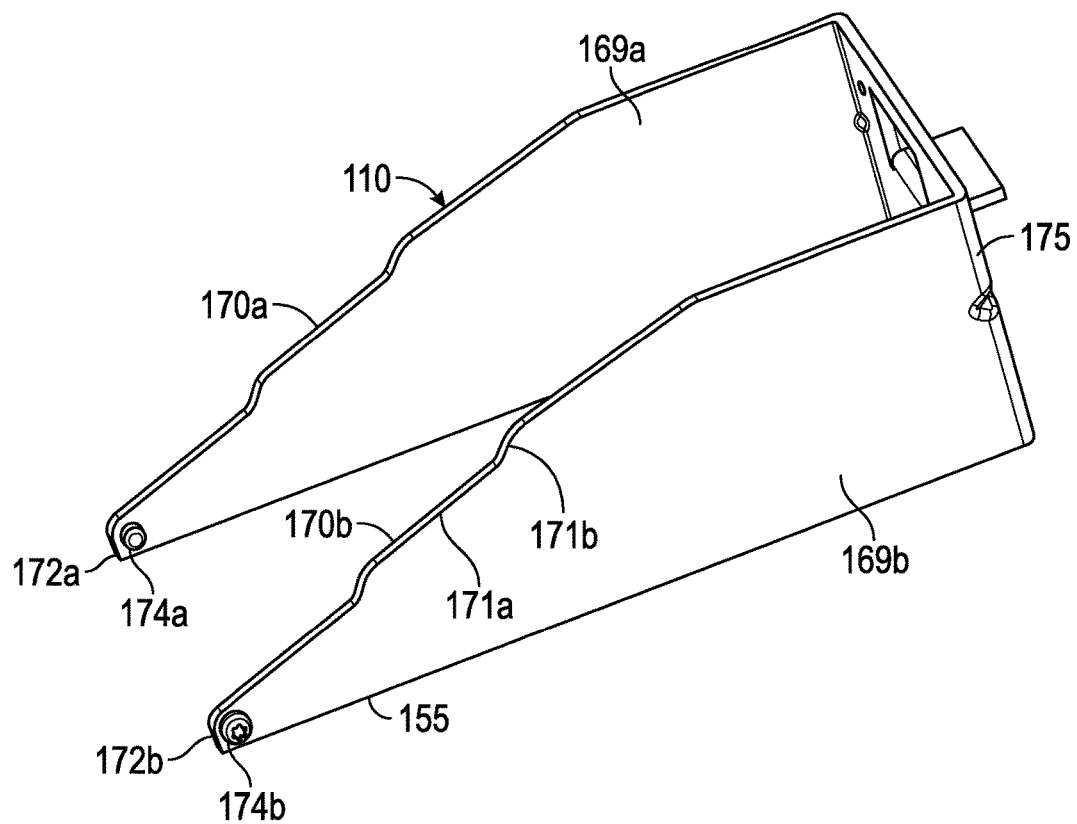
FIG. 5 is a perspective view of a ramp member according to the inventive concepts disclosed herein.
Figure 6:
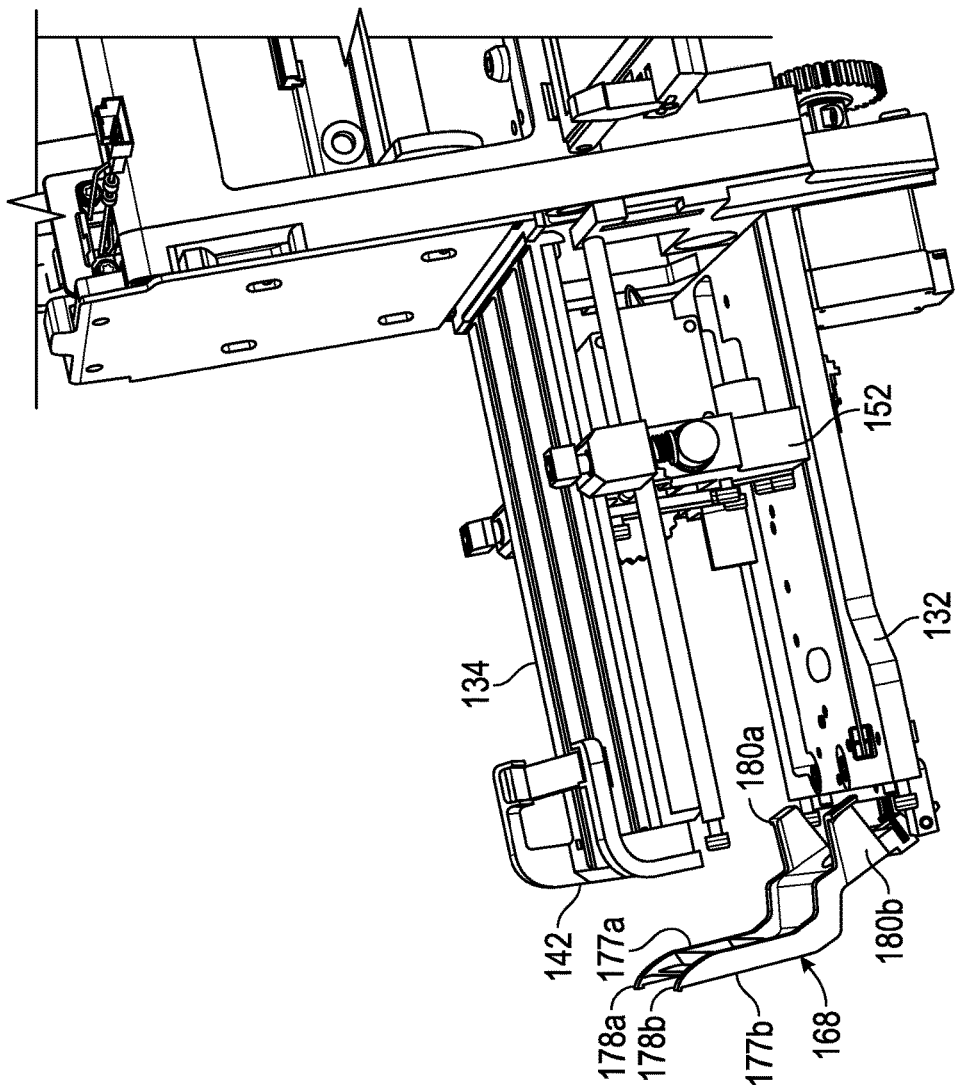
FIG. 6 is a partial perspective view of the analyzer of FIG. 1, with the ramp member not shown, for clarity.

Referring now to FIGS. 4-6, the waste ramp assembly 110 may include the one or more ramp member 155, and an optional comb 168.

The ramp member 155 may be attached to the carriage 152 in any suitable manner, and may have two sides 169a and 169b and spaced apart a sloped surfaces 170a and 170b, ends 172a and 172b, one or more comb-engaging protrusions 174a and 174b, and a flange 175 connected to the sides 169a and 169b. For example, the ramp member 155 may be attached to the carriage 152 via fasteners, bolts, screws, adhesives, welds, joints, seams, brackets, shims, and combinations thereof. The ramp member 155 may be constructed of more than one component that are connected together, or may be made of unitary construction. Further, the ramp member 155 and the carriage 152 may be implemented as a unitary component in some exemplary embodiments.

The ramp member 155 may move with the carriage 152, such that the ramp member 155 is movable between an extended position where the ramp member 155 extends laterally from the edge 142 and below the travel surface 134, and a retracted position where the ends 172a and 172b of the ramp member 155 are substantially completely positioned below the travel surface 134, for example. It is to be understood that in some exemplary embodiments, the ramp member 155 may be in the retracted position when about two-thirds of the length of the ramp member 155 is positioned below the travel surface 134.

As will be appreciated by persons of ordinary skill in the art having the benefit of the instant disclosure, in some exemplary embodiments the ramp member 155 may be operably coupled with any desired mechanism configured to move the ramp member 155 between the extended position and the retracted position, such as an actuator, a motor, a movable carriage, a ratcheting mechanism, and combinations thereof. Further, while one ramp member 155 is shown, in some exemplary embodiments any desired number of ramp members 155 may be used, such as 2, 3, 4, 5, 6, or more ramp members 155, for example.

The sloped surfaces 170a and 170b can be configured to allow a reagent card 114 to slide thereon, as will be described below. The sloped surfaces 170a and 170b may have any desired slope, angle, or slant, for example, and may include a first portion 171a having a first slope, and a second portion 171b having a second slope. The first portion 171a and the second portion 171b may be alternated such that a stepped sloped surface 170a or a sloped surface 170b is formed in some exemplary embodiments. The sloped surfaces 170a and 170b may have any desired slope (or angle) so as to allow a reagent card 114 to slide over sloped surfaces 170a and 170b of the ramp member 155, such as a slope (or angle) varying from about 0° to about 60°, for example, including any ranges and sub-ranges therebetween.

The sides 169a and 169b may have any desired cross-section, such as being substantially square, substantially rectangular, substantially circular, oval, irregular, triangular, and combinations thereof, for example. Further, the sloped surfaces 170a and 170b may be coated with any desired friction-reducing coating, such as nickel-polytetrafluoroethylene, or any other suitable coating, for example.

In some exemplary embodiments of the inventive concepts disclosed herein, one or more rollers (not shown) may be incorporated with the sloped surfaces 170a and 170b such that the one or more rollers may roll under the reagent card 114 as the reagent card 114 slides over the sloped surface 170.

The ends 172a and 172b may be rounded. The one or more optional comb-engaging protrusions 174a and 174b may be connected to the sides 169a and 169b adjacent to the ends 172a and 172b. The comb-engaging protrusion 174a and 174b may be configured to engage the optional comb 168 as will be described below.

The ramp member 155 may be constructed of any desired material, such as aluminum, stainless steel, titanium, metals, alloys, non-metals, plastics, resins, ceramics, and combinations thereof, for example.

As shown in FIG. 6, the comb 168 may be pivotably connected to the support 132 below the edge 142, so that the comb 168 may be laterally offset from the edge 142 and may pivot relative to the edge 142 between a deployed position and a retracted position. The comb 168 may include spaced apart sides 177a and 177b with the sides 177a and 177b defining ridges 178a and 178a. The ridges 178a and 178b are substantially below the travel surface 134 when the comb 168 is in the retracted position and at least partially above the sloped surfaces 170a and 170b of the ramp member 155 when the comb 168 is in the deployed position and the ramp member 155 is in the extended position. The comb 168 may be biased in the deployed position in some exemplary embodiments, such as via a spring (not shown) or any other desired mechanism.

The sides 177a and 177b of the comb 168 may further include one or more tabs 180. The one or more tabs 180 may be configured and positioned to engage to the one or more comb-engaging protrusions 174a and 174b of the ramp member 155, to allow the ramp member 155 to move the comb 168 to the deployed position as the ramp member 155 approaches its substantially retracted position. The comb-engaging protrusions 174a and 174b may engage the one or more tabs 180 and may pivot the comb 168 relative to the support 132 so as to move the comb 168 between the deployed and retracted positions, for example.

It is to be understood, however, that the comb 168 may be deployed by any other suitable mechanism, and that the comb 168 may be omitted in some exemplary embodiments of the inventive concepts disclosed herein.

As will be readily appreciated by a person of ordinary skill in the art, the comb 168 may include a ratchet-type mechanism to prevent the one or more reagent cards 114 from sliding back up the ramp member 155 when the comb 168 is deployed, and to allow the one or more reagent cards 114 to fall substantially flat into the waste receptacle 112, for example, as will be described below.

The comb 168 may be constructed of any desired material, such as plastics, metals, alloys, resins, ceramics, and combinations thereof, for example.

Referring back to FIG. 2, the waste receptacle 112 may include a substantially flat bottom 182 and a side 184 extending from the bottom 182 to define a waste cavity 185. The waste receptacle 112 may be implemented as a container or a drawer, for example, and may be sized and configured so that the waste cavity 185 may receive one or more reagent card 114. The one or more reagent card 114 may be stacked on and supported by the bottom 182 thereof, for example. The waste receptacle 112 may be supported laterally offset from the edge 142 and below the travel surface 134 and below the waste ramp assembly 110, for example, such that one or more reagent cards 114 may fall off the edge 142 of the travel surface 134, and may be stacked onto the bottom 182 of the waste receptacle 112 by the waste ramp assembly 110, for example. In some exemplary embodiments, the ramp member 155 may be spaced at a first distance from the side 184, which first distance may be less than the length of the reagent card 114, when the ramp member 155 is in the substantially extended position.

Further, the ramp member 155 may be spaced at a second distance from the side 184, which second distance may be substantially equal to, or greater than, the length of the reagent card 114, when the ramp member 155 is in the substantially retracted position, for example.

The bottom 182 may be configured to support one or more reagent cards 114 thereon, and may be implemented as a side, one or more tabs, one or more beams, struts, protrusions, and combinations thereof, for example.

The waste receptacle 112 may be removable from the analyzer 100, or the interior of the waste receptacle 112 may be accessible (e.g., via a door) to remove one or more reagent cards 114 therefrom, for example. An optional optical sensor (not shown) may be implemented with the waste receptacle 112 to alert a user when the waste receptacle 112 is substantially full of reagent cards 114, so that the user may remove the reagent cards 114 and dispose of them as desired.

The waste receptacle 112 may be constructed of any suitable material, and may include one or more containment lining (not shown), for example.

Figure 7:
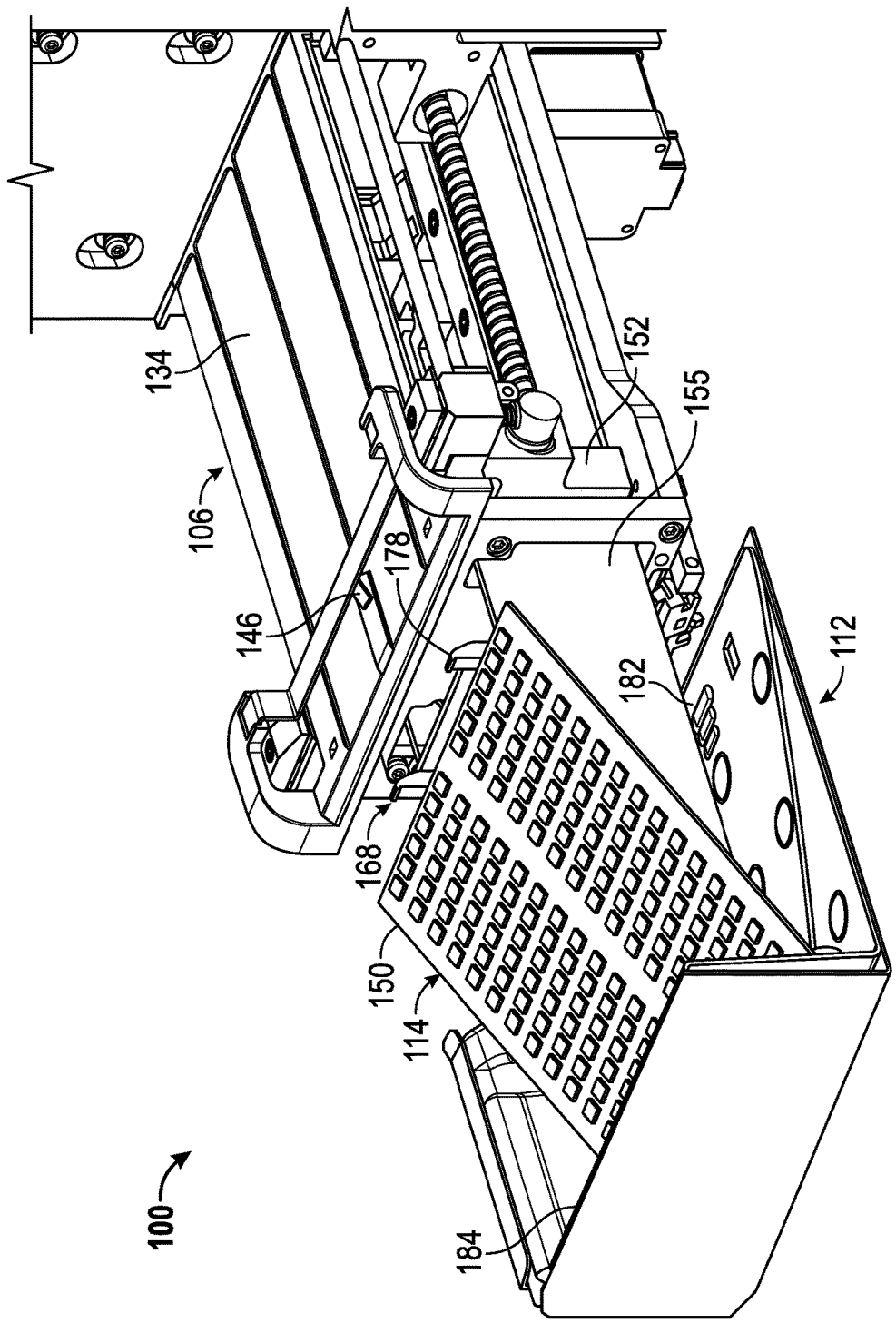
FIG. 7 is a partial perspective view of the analyzer of FIG. 1, showing a reagent card positioned on an extended ramp member.
Figure 8:
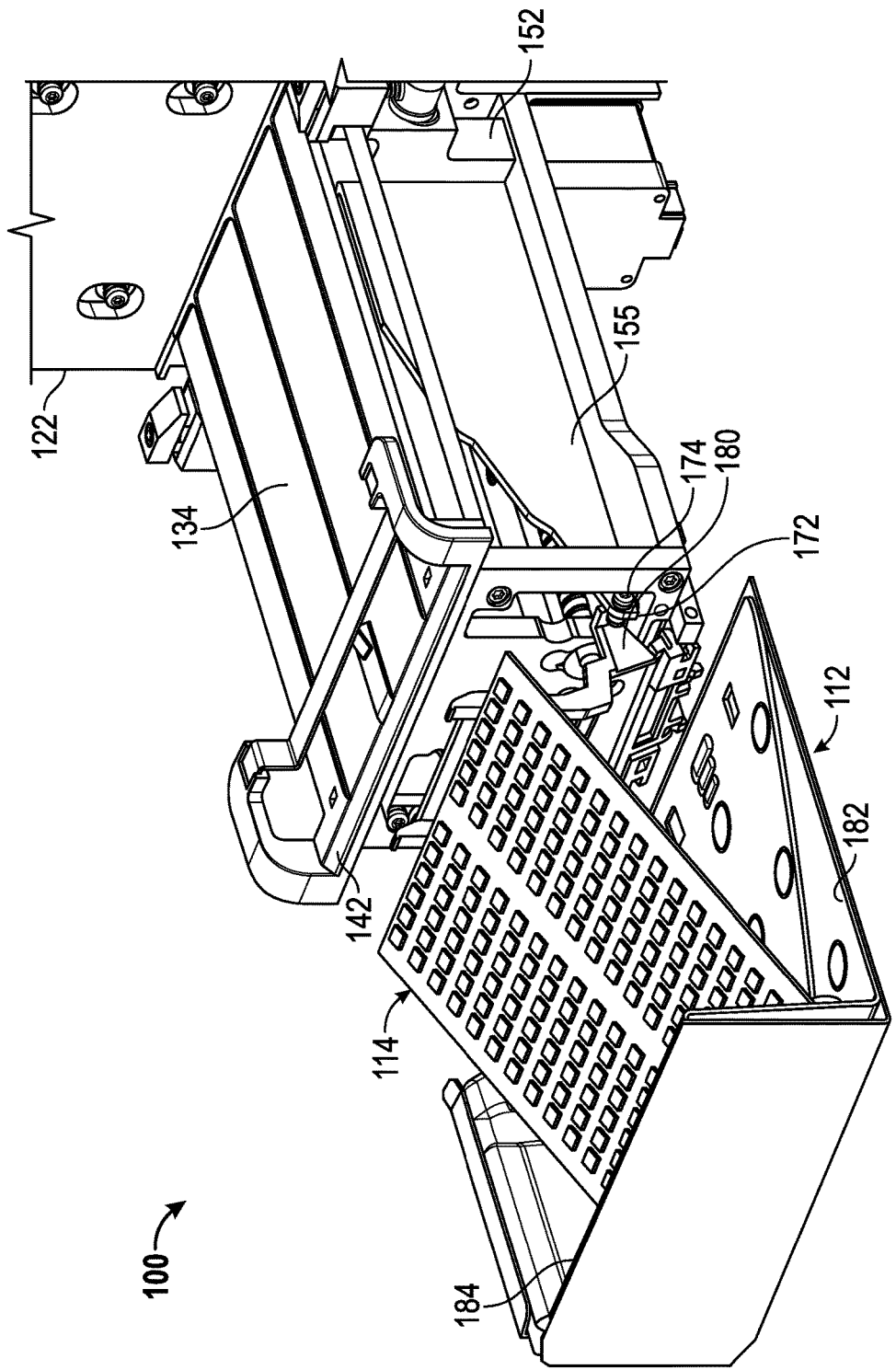
FIG. 8 is a partial perspective view of the analyzer of FIG. 1, with the ramp member shown in a partially retracted position and the reagent card being held in place by a comb according to the inventive concepts disclosed herein.
Figure 9:
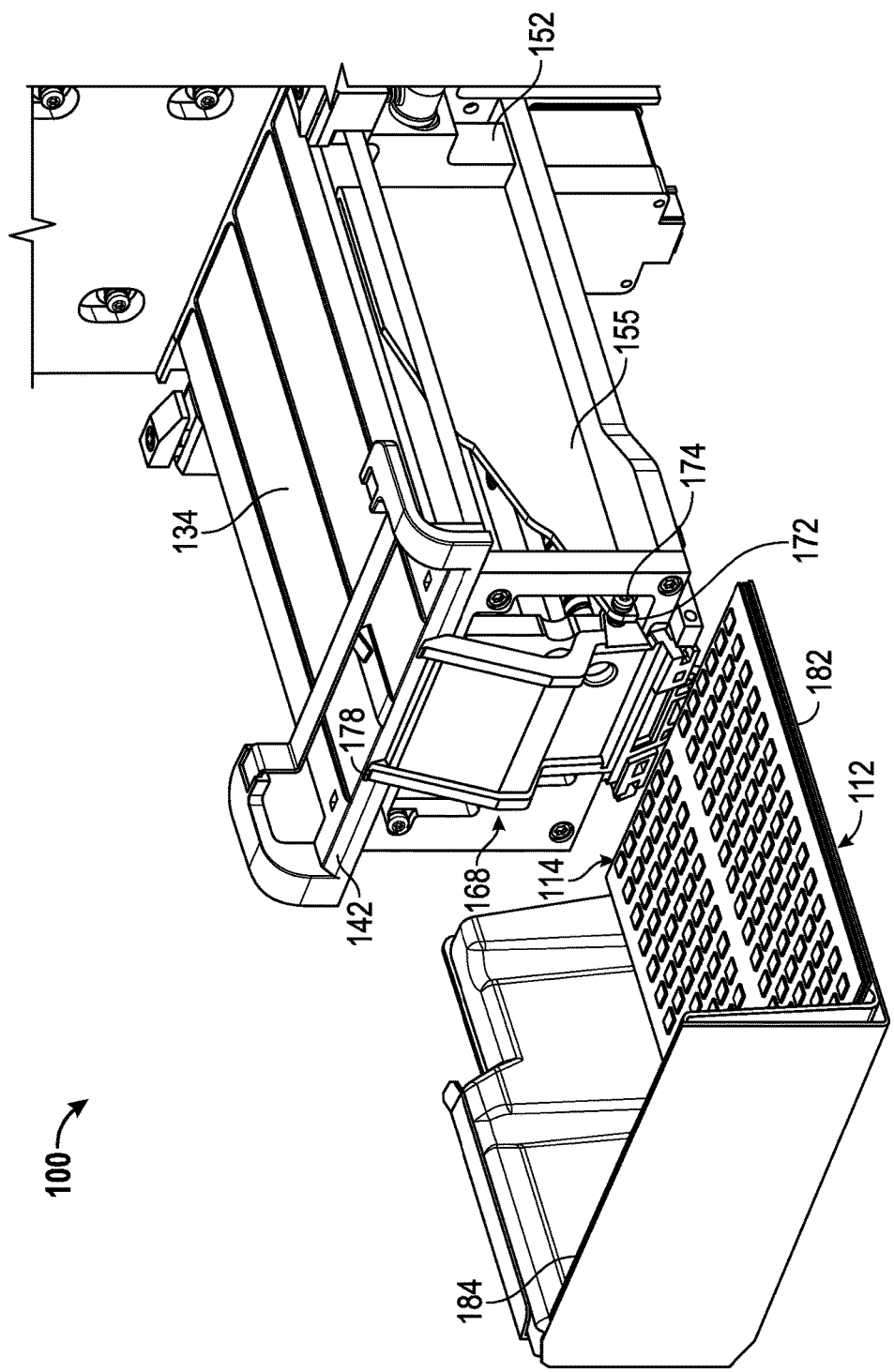
FIG. 9 is a partial perspective view of the analyzer of FIG. 1, with the waste ramp assembly shown in a retracted position, and the card shown positioned on another reagent card at the bottom of a waste receptacle according to the inventive concepts disclosed herein.

Referring now to FIGS. 7-9, in operation an analyzer 100 may operate as follows: A reagent card 114 may be advanced past the edge 142 (FIG. 2) by the mover assembly 108. The leading end 148 of the reagent card may pass between the travel surface 134 and the spring 144, such that the tab 146 compresses the reagent card 114 against the travel surface 134, for example. As the trailing end 150 of the reagent card 114 clears the tab 146, the reagent card 114 may fall onto the substantially extended ramp member 155 as shown in FIG. 7. For example, the ramp member 155 may extend into the waste receptacle 112 a distance from the side 184 of less than the length of the reagent card 114. As the reagent card 114 falls onto the ramp member 155 (e.g., under gravity), the reagent card slides over the sloped surface 170 and over the ridge 178 of the comb 168 (the comb 168 being in the deployed position), such that the leading end 148 of the reagent card 114 comes into contact with the side 184 of the waste receptacle 112, for example.

As shown in FIG. 8, the trailing end 150 of the reagent card 114 may be engaged by the comb 168 so that the comb 168 may substantially maintain the position of the reagent card 114 as the ramp member 155 is retracted such that the reagent card 114 is substantially supported by the side 184 and at least partially by the comb 168 as the ramp member 155 is retracted via the carriage 152 moving towards the gate 122, for example.

As the ramp member 155 approaches the retracted position (e.g., being retracted to a distance from the side 184 substantially equal to or greater than the length of the reagent card 114), the comb-engaging protrusions 174a and 174b engage the tabs 180a and 180b of the comb 168 and pull the comb 168 into its retracted position as the ramp member 155 reaches its retracted position. As the comb 168 is pulled toward the retracted position, the comb 168 disengages the trailing end 150 of the reagent card 114, which causes the reagent card 114 to fall substantially flat onto the bottom 182 of the waste receptacle 112. Two or more reagent cards 114 may be stacked onto one another in this manner as shown in FIG. 9, for example.

As one or more reagent cards 114 are stacked into the waste receptacle 112, the waste receptacle 112 may be removed from the analyzer 100, or the waste cavity 185 of the waste receptacle 112 may be accessed, and the one or more used reagent cards 114 may be disposed of in any desired manner, for example.

As will be appreciated by a person of ordinary skill in the art, the comb 168 may be omitted in some exemplary embodiments of the inventive concepts disclosed herein, and the one or more reagent card 114 may be stacked onto the bottom 182 or onto one another via the ramp member 155 substantially as described above.

It is to be understood that the steps disclosed herein may be performed simultaneously or in any desired order, and may be carried out by a human, or by a machine, and combinations thereof, for example. For example, one or more of the steps disclosed herein may be omitted, one or more steps may be further divided in one or more sub-steps, and two or more steps or sub-steps may be combined in a single step, for example. Further, in some exemplary embodiments, one or more steps may be repeated one or more times, whether such repetition is carried out sequentially or interspersed by other steps or sub-steps. Additionally, one or more other steps or sub-steps may be carried out before, after, or between the steps disclosed herein, for example.

From the above description, it is clear that the inventive concepts disclosed herein are well adapted to carry out the objects and to attain the advantages mentioned herein as well as those inherent in the inventive concepts disclosed herein. While exemplary embodiments of the inventive concepts disclosed herein have been described for purposes of this disclosure, it will be understood that numerous changes may be made which will readily suggest themselves to those skilled in the art and which are accomplished within the scope of the inventive concepts disclosed and as defined in the appended claims.

What is claimed is:

1. A method, comprising:
    advancing a reagent card having a leading end and a trailing end along a card travel surface of an automated analyzer and past an edge of the card travel surface so the reagent card falls onto a sloped surface of a ramp member positioned within a waste cavity of a waste receptacle and the leading end of the reagent card contacts a side of the waste receptacle extending from a bottom of the waste receptacle;
    removing the ramp member from the waste cavity;
    engaging the trailing end of the reagent card with a comb in a deployed position so the reagent card is supported by the comb and the side of the waste receptacle as the ramp member is removed from the waste cavity; and
    moving the comb to a retracted position to disengage the trailing end of the reagent card so the reagent card falls onto the bottom of the waste receptacle.

2. The method of claim 1, wherein the reagent card is a first reagent card, and wherein the method further comprises:
    moving the ramp member into the waste cavity;
    advancing a second reagent card having a leading end and a trailing end along the card travel surface and past the edge of the card travel surface so the second reagent card falls onto the sloped surface of the ramp member and the leading end of the second reagent card contacts the side of the waste receptacle;
    removing the ramp member from the waste cavity;
    engaging the trailing end of the second reagent card with the comb in the deployed position so the second reagent card is supported by the comb and the side of the waste receptacle as the ramp member is removed from the waste cavity; and
    moving the comb to the retracted position to disengage the trailing end of the second reagent card so the second reagent card falls onto first reagent card.

3. The method of claim 2, further comprising reading the first and second reagent cards as the first and second reagent cards are advanced along the card travel surface.

4. The method of claim 2, further comprising applying samples to the first and second reagent cards as the first and second reagent cards are advanced along the card travel surface.

5. The method of claim 2, wherein the comb is in the deployed position during the step of advancing the first reagent card.

6. The method of claim 2, wherein the comb is in the deployed position during the steps of advancing the first reagent card and advancing the second reagent card.

* * * * *